United States Patent
Westbye et al.

(10) Patent No.: US 8,372,044 B2
(45) Date of Patent: *Feb. 12, 2013

(54) SYRINGE WITH NEEDLE GUARD INJECTION DEVICE

(75) Inventors: Lars Tommy Westbye, Carlsbad, CA (US); Philip Dowds, San Diego, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 775 days.

This patent is subject to a terminal disclaimer.

(21) Appl. No.: 11/133,634

(22) Filed: May 20, 2005

(65) Prior Publication Data

US 2006/0264825 A1    Nov. 23, 2006

(51) Int. Cl.
*A61M 5/32* (2006.01)
*A61M 5/00* (2006.01)

(52) U.S. Cl. ........ 604/198; 128/919; 604/110; 604/192; 604/197; 604/263

(58) Field of Classification Search .......... 604/192, 604/198, 210, 110, 181, 187, 218, 197, 227, 604/263; 128/919, 917
See application file for complete search history.

(56) References Cited

U.S. PATENT DOCUMENTS

| | | |
|---|---|---|
| 827,383 A | 7/1906 | McElroy et al. |
| 1,652,894 A | 12/1927 | Gunther |
| 1,921,034 A | 8/1933 | Lamarche |
| 2,432,605 A | 12/1947 | Barach |
| 2,571,653 A | 10/1951 | Bastien |
| 2,586,581 A | 2/1952 | Tschischeck |
| 2,895,474 A | 7/1959 | Reznek |
| 2,925,083 A | 2/1960 | Craig |
| 3,046,985 A | 7/1962 | Saenz |
| 3,306,290 A | 2/1967 | Weltman |

(Continued)

FOREIGN PATENT DOCUMENTS

| | | |
|---|---|---|
| EP | 0 405 039 A1 | 1/1991 |
| EP | 0467173 A | 1/1992 |

(Continued)

OTHER PUBLICATIONS

U.S. Patent and Trademark Office, Official Gazette, vol. 1223, No. 2, pp. 818, 819, and 820, dated Jun. 8, 1999.

(Continued)

*Primary Examiner* — Kevin C Sirmons
*Assistant Examiner* — Shefali Patel
(74) *Attorney, Agent, or Firm* — Dickstein Shapiro LLP; Kenneth S. Roberts

(57) ABSTRACT

The present invention provides an injection device including a syringe having a distal end for receiving a needle, and a plunger inserted into a proximal end. A guard is slidable on the syringe, has a proximal end, a distal end, and is biased from a first position wherein the needle is exposed toward a second position wherein the guard covers the needle. The syringe includes a body having a central cylindrical opening for receiving a medicine and the plunger, and further includes a pair of longitudinally extending members on opposite sides of the body. The injection device includes cooperating detents for retaining the guard and syringe in the first and second positions. A latch member is engageable by the plunger as the plunger is depressed to release the cooperating detents. Upon release, a spring element biases the guard toward the second position.

9 Claims, 4 Drawing Sheets

U.S. PATENT DOCUMENTS

| | | |
|---|---|---|
| 3,583,230 A | 6/1971 | Patterson |
| 3,583,399 A | 6/1971 | Ritsky |
| 3,878,846 A | 4/1975 | Rimbaud |
| 3,885,562 A | 5/1975 | Lampkin |
| 3,930,499 A | 1/1976 | Rimbaud |
| 3,943,927 A | 3/1976 | Norgren |
| 3,973,554 A | 8/1976 | Tipton |
| 4,018,223 A | 4/1977 | Ethington |
| 4,022,207 A | 5/1977 | Citrin |
| 4,048,997 A | 9/1977 | Raghavachari et al. |
| 4,171,699 A | 10/1979 | Jones et al. |
| 4,333,456 A | 6/1982 | Webb |
| 4,333,457 A | 6/1982 | Margulies |
| 4,356,822 A | 11/1982 | Winstead-Hall |
| 4,381,779 A | 5/1983 | Margulies |
| 4,425,120 A | 1/1984 | Sampson et al. |
| 4,425,230 A | 1/1984 | Andress et al. |
| 4,540,405 A | 9/1985 | Miller et al. |
| 4,573,976 A | 3/1986 | Sampson et al. |
| 4,592,744 A | 6/1986 | Jagger et al. |
| 4,601,711 A | 7/1986 | Ashbury et al. |
| 4,631,057 A | 12/1986 | Mitchell |
| 4,643,199 A | 2/1987 | Jennings, Jr. et al. |
| 4,655,751 A | 4/1987 | Harbaugh |
| 4,681,567 A | 7/1987 | Masters et al. |
| 4,690,676 A | 9/1987 | Moulding, Jr. et al. |
| 4,702,738 A | 10/1987 | Spencer |
| 4,723,943 A | 2/1988 | Spencer |
| 4,728,321 A | 3/1988 | Chen |
| 4,737,144 A | 4/1988 | Choksi |
| 4,738,663 A | 4/1988 | Bogan |
| 4,743,234 A | 5/1988 | Leopoldi et al. |
| 4,747,831 A | 5/1988 | Kulli |
| 4,762,516 A | 8/1988 | Luther et al. |
| 4,767,413 A | 8/1988 | Haber et al. |
| 4,772,272 A | 9/1988 | McFarland |
| 4,795,443 A | 1/1989 | Permenter et al. |
| 4,801,295 A | 1/1989 | Spencer |
| 4,813,426 A | 3/1989 | Haber et al. |
| 4,820,275 A | 4/1989 | Haber et al. |
| 4,832,696 A | 5/1989 | Luther et al. |
| 4,840,185 A | 6/1989 | Hernandez |
| 4,850,961 A | 7/1989 | Wanderer et al. |
| 4,850,994 A | 7/1989 | Zerbst et al. |
| 4,869,249 A | 9/1989 | Crossman et al. |
| 4,871,355 A | 10/1989 | Kikkawa |
| 4,874,384 A | 10/1989 | Nunez |
| 4,878,902 A | 11/1989 | Wanderer et al. |
| 4,892,523 A | 1/1990 | Haber et al. |
| 4,898,590 A | 2/1990 | Andors |
| 4,900,310 A | 2/1990 | Ogle, II |
| 4,911,693 A | 3/1990 | Paris |
| 4,915,701 A | 4/1990 | Halkyard |
| 4,915,702 A | 4/1990 | Haber |
| 4,917,669 A | 4/1990 | Bonaldo |
| 4,917,673 A | 4/1990 | Coplin |
| 4,923,445 A | 5/1990 | Ryan |
| 4,923,447 A | 5/1990 | Morgan |
| 4,927,416 A | 5/1990 | Tomkiel |
| 4,932,947 A | 6/1990 | Cardwell |
| 4,935,016 A | 6/1990 | Delco |
| 4,938,745 A | 7/1990 | Sagstetter |
| 4,946,446 A | 8/1990 | Vadher |
| 4,946,447 A | 8/1990 | Hardcastle et al. |
| 4,955,868 A | 9/1990 | Klein |
| 4,957,490 A | 9/1990 | Byrne et al. |
| 4,969,877 A | 11/1990 | Kornberg |
| 4,974,603 A | 12/1990 | Jacobs |
| 4,990,141 A | 2/1991 | Byrne et al. |
| 5,000,744 A | 3/1991 | Hoffman et al. |
| 5,002,537 A | 3/1991 | Hoffman et al. |
| 5,007,903 A | 4/1991 | Ellard |
| 5,013,301 A | 5/1991 | Marotta, Jr. et al. |
| 5,013,305 A | 5/1991 | Opie et al. |
| 5,030,209 A | 7/1991 | Wanderer et al. |
| 5,033,650 A | 7/1991 | Colin et al. |
| 5,045,066 A | 9/1991 | Scheuble et al. |
| 5,057,087 A | 10/1991 | Harmon |
| 5,059,184 A | 10/1991 | Dyke |
| 5,059,185 A | 10/1991 | Ryan |
| 5,067,490 A | 11/1991 | Haber |
| 5,067,945 A | 11/1991 | Ryan et al. |
| 5,069,225 A | 12/1991 | Okamura |
| 5,070,884 A | 12/1991 | Columbus et al. |
| 5,070,885 A | 12/1991 | Bonaldo |
| 5,085,639 A | 2/1992 | Ryan |
| 5,086,780 A | 2/1992 | Schmitt |
| 5,086,982 A | 2/1992 | Ryan |
| 5,088,982 A | 2/1992 | Ryan |
| 5,088,986 A | 2/1992 | Nusbaum |
| 5,088,988 A | 2/1992 | Talonn et al. |
| 5,098,382 A | 3/1992 | Haber et al. |
| 5,100,427 A | 3/1992 | Crossman et al. |
| 5,100,428 A | 3/1992 | Mumford |
| 5,104,380 A | 4/1992 | Holman et al. |
| 5,104,386 A | 4/1992 | Alzain |
| 5,106,379 A | 4/1992 | Leap |
| 5,108,376 A | 4/1992 | Bonaldo |
| 5,108,378 A | 4/1992 | Firth et al. |
| 5,112,307 A | 5/1992 | Haber et al. |
| 5,116,319 A | 5/1992 | Van Den Haak |
| 5,120,311 A | 6/1992 | Sagstetter et al. |
| 5,131,405 A | 7/1992 | Burns |
| 5,137,521 A | 8/1992 | Wilkins |
| 5,141,500 A | 8/1992 | Hake |
| 5,147,326 A | 9/1992 | Talonn et al. |
| 5,154,699 A | 10/1992 | Ryan |
| 5,163,917 A | 11/1992 | Huefner et al. |
| 5,176,656 A | 1/1993 | Bayless |
| 5,176,657 A | 1/1993 | Shields |
| 5,201,708 A | 4/1993 | Martin |
| 5,201,720 A | 4/1993 | Borgia et al. |
| 5,207,646 A | 5/1993 | Brunel |
| 5,215,535 A | 6/1993 | Gettig et al. |
| 5,219,339 A | 6/1993 | Saito |
| 5,242,416 A | 9/1993 | Hutson |
| 5,242,420 A | 9/1993 | Martin |
| 5,246,011 A | 9/1993 | Caillouette |
| 5,259,841 A | 11/1993 | Hohendorfer et al. |
| 5,266,072 A | 11/1993 | Utterberg et al. |
| 5,269,766 A | 12/1993 | Haber et al. |
| 5,273,541 A | 12/1993 | Malenchek |
| 5,279,581 A | 1/1994 | Firth et al. |
| 5,300,030 A | 4/1994 | Crossman et al. |
| 5,328,485 A | 7/1994 | Moreno et al. |
| 5,330,438 A | 7/1994 | Gollobin et al. |
| 5,336,185 A | 8/1994 | Lynch et al. |
| 5,342,320 A | 8/1994 | Cameron |
| 5,344,407 A | 9/1994 | Ryan |
| 5,372,590 A | 12/1994 | Haber |
| 5,385,557 A | 1/1995 | Thompson |
| 5,407,431 A | 4/1995 | Botich et al. |
| 5,417,660 A | 5/1995 | Martin |
| 5,433,712 A | 7/1995 | Stiles et al. |
| 5,437,639 A | 8/1995 | Malenchek |
| 5,437,647 A * | 8/1995 | Firth et al. .................. 604/110 |
| 5,445,620 A | 8/1995 | Haber et al. |
| 5,492,536 A | 2/1996 | Mascia |
| 5,496,286 A | 3/1996 | Stiehl et al. |
| 5,498,244 A | 3/1996 | Eck |
| 5,501,672 A | 3/1996 | Firth et al. |
| 5,514,107 A | 5/1996 | Haber et al. |
| 5,522,812 A | 6/1996 | Talonn |
| 5,531,706 A | 7/1996 | De la Fuente |
| 5,554,122 A | 9/1996 | Emanuel |
| 5,562,624 A * | 10/1996 | Righi et al. .................. 604/110 |
| 5,562,626 A | 10/1996 | Sanpietro |
| 5,569,211 A | 10/1996 | Lekhgolts et al. |
| 5,571,089 A | 11/1996 | Crocker |
| 5,573,508 A | 11/1996 | Thornton |
| 5,573,512 A | 11/1996 | van den Haak |
| 5,573,513 A | 11/1996 | Wozencroft |
| 5,575,771 A | 11/1996 | Walinsky |
| 5,599,309 A | 2/1997 | Marshall et al. |
| 5,611,783 A | 3/1997 | Mikkelsen |
| 5,611,809 A | 3/1997 | Marshall et al. |
| 5,616,134 A | 4/1997 | Firth et al. |

| | | | |
|---|---|---|---|
| 5,624,400 A | 4/1997 | Firth et al. | |
| 5,643,214 A | 7/1997 | Marshall et al. | |
| 5,674,203 A | 10/1997 | Lewandowski | |
| 5,695,475 A | 12/1997 | Best, Jr. et al. | |
| 5,709,663 A | 1/1998 | Younkes | |
| 5,716,340 A | 2/1998 | Schweich, Jr. et al. | |
| 5,762,635 A | 6/1998 | Pace et al. | |
| 5,855,839 A | 1/1999 | Brunel | |
| 5,928,205 A | 7/1999 | Marshall | |
| 5,980,487 A | 11/1999 | Jones et al. | |
| 5,989,226 A | 11/1999 | Hymanson | |
| 6,004,296 A | 12/1999 | Jansen et al. | |
| 6,015,402 A | 1/2000 | Sahota | |
| 6,017,330 A | 1/2000 | Hitchins et al. | |
| 6,030,366 A | 2/2000 | Mitchell | |
| 6,077,247 A | 6/2000 | Marshall et al. | |
| 6,086,568 A | 7/2000 | Caizza | |
| 6,102,893 A * | 8/2000 | Aneas | 604/110 |
| 6,159,181 A | 12/2000 | Crossman et al. | |
| 6,159,184 A | 12/2000 | Perez et al. | |
| 6,171,283 B1 * | 1/2001 | Perez et al. | 604/192 |
| 6,186,980 B1 | 2/2001 | Brunel | |
| 6,193,695 B1 | 2/2001 | Rippstein, Jr. | |
| 6,203,530 B1 | 3/2001 | Stewart | |
| 6,206,853 B1 | 3/2001 | Bonnet | |
| RE37,439 E | 11/2001 | Firth et al. | |
| 6,319,233 B1 | 11/2001 | Jansen et al. | |
| 6,319,234 B1 | 11/2001 | Restelli et al. | |
| 6,344,032 B1 | 2/2002 | Perez et al. | |
| 6,416,323 B1 | 7/2002 | Grenfell et al. | |
| 6,425,880 B1 | 7/2002 | Marshall | |
| 6,461,333 B1 | 10/2002 | Frezza | |
| 4,923,477 A1 | 2/2003 | Hansen | |
| 6,550,967 B2 | 4/2003 | Hedaya | |
| 6,613,022 B1 | 9/2003 | Doyle | |
| 6,623,459 B1 | 9/2003 | Doyle | |
| 6,719,730 B2 | 4/2004 | Jansen et al. | |
| 6,719,736 B2 | 4/2004 | Collins et al. | |
| 6,752,798 B2 | 6/2004 | McWethy et al. | |
| 6,846,302 B2 * | 1/2005 | Shemesh et al. | 604/110 |
| 6,976,976 B2 * | 12/2005 | Doyle | 604/198 |
| 2001/0005781 A1 | 6/2001 | Amark | |
| 2002/0032412 A1 | 3/2002 | Riemelmoser | |
| 2002/0045864 A1 | 4/2002 | Perez et al. | |
| 2002/0169421 A1 | 11/2002 | McWethy et al. | |
| 2002/0193746 A1 | 12/2002 | Chevallier | |
| 2003/0069545 A1 | 10/2003 | Doyle | |
| 2003/0187402 A1 * | 10/2003 | Doyle | 604/198 |

FOREIGN PATENT DOCUMENTS

| | | |
|---|---|---|
| EP | 0 555974 A1 | 8/1993 |
| EP | 0 680 767 A1 | 11/1995 |
| EP | 0 740 942 A1 | 11/1996 |
| EP | 0 864 335 A2 | 9/1998 |
| EP | 0 940 153 A1 | 9/1999 |
| EP | 0 966 983 A1 | 12/1999 |
| EP | 1371382 A | 12/2003 |
| EP | 1284769 B1 | 11/2005 |
| FR | 2 654 346 A1 | 5/1991 |
| FR | 2 782 011 A1 | 8/1998 |
| FR | 2 764 195 A1 | 12/1998 |
| FR | 2 788 984 A1 | 1/1999 |
| FR | 2 788 985 A1 | 7/1999 |
| FR | 2 778 853 A1 | 11/1999 |
| FR | 2 799 976 A1 | 4/2001 |
| FR | 2 801 795 A1 | 6/2001 |
| GB | 2 283 425 A | 5/1995 |
| WO | WO 88/02297 A1 | 4/1988 |
| WO | WO 91/18634 A1 | 12/1991 |
| WO | WO 93/00949 A1 | 1/1993 |
| WO | WO 93/17732 A2 | 9/1993 |
| WO | WO 95/04565 A1 | 2/1995 |
| WO | WO 98/35714 A1 | 8/1998 |
| WO | WO 99/16489 A1 | 4/1999 |
| WO | WO 99/17823 A1 | 4/1999 |
| WO | WO 99/32177 A1 | 7/1999 |
| WO | WO 99/37343 A1 | 7/1999 |
| WO | WO 99/37345 A1 | 7/1999 |
| WO | WO 99/56805 | 11/1999 |
| WO | WO 00/76565 A1 | 1/2000 |
| WO | WO 00/33900 A1 | 6/2001 |
| WO | WO 01/41841 A2 | 6/2001 |
| WO | WO 01/80931 A2 | 11/2001 |
| WO | WO 01/85239 A | 11/2001 |
| WO | WO 01/85239 A2 | 11/2001 |
| WO | WO 03/013632 A2 | 2/2003 |
| WO | WO 03/082385 A | 10/2003 |
| WO | WO 03/082386 A | 10/2003 |
| WO | WO 2006/050304 A | 11/2006 |

OTHER PUBLICATIONS

U.S. Patent and Trademark Office, Official Gazette, vol. 1223, No. 4, pp. 2156, 2157, and 2575, dated Jun. 22, 1999.
U.S. Patent and Trademark Office, Official Gazette, vol. 1224, No. 1, pp. 303, 305, and 306 dated Jul. 6, 1999.
U.S. Patent and Trademark Office, Official Gazette, vol. 1224, No. 4, p. 3115 and 3404, dated Jul. 27, 1999.
U.S. Patent and Trademark Office, Official Gazette, vol. 1232, No. 1, pp. 381, 382, 384, 385, 386, and 387, dated Mar. 7, 2000.
U.S. Patent and Trademark Office, Official Gazette, vol. 1232, No. 2, pp. 1507, 1508, and 1509, dated Mar. 14, 2000.
U.S. Patent and Trademark Office, Official Gazette, vol. 1232, No. 3, p. 2532, dated Mar. 21, 2000 Book 2 of 2 Books.
U.S. Patent and Trademark Office, Official Gazette, vol. 1232, No. 4, p. 3505, dated Mar. 28, 2000.
U.S. Patent and Trademark Office, Official Gazette, vol. 1234, No. 4, pp. 3543 and 3829, May 23, 2000.
U.S. Patent and Trademark Office, Official Gazette, vol. 1235, No. 2, pp. 1234, 1443, and 1444, dated Jun. 13, 2000.
U.S. Patent and Trademark Office, Official Gazette, vol. 1235, No. 3, pp. 2456 and 2457, dated Jun. 20, 2000.
U.S. Patent and Trademark Office, Official Gazette, vol. 1236, No. 1, p. 443, dated Jul. 4, 2000.
U.S. Patent and Trademark Office, Official Gazette, vol. 1236, No. 2, pp. 1625 and 1626, dated Jul. 11, 2000.
U.S. Patent and Trademark Office, Official Gazette, vol. 1236, No. 3, pp. 2873 and 2874, dated Jul. 18, 2000.
U.S. Patent and Trademark Office, Official Gazette, vol. 1236, No. 4, pp. 3963 and 3964, dated Jul. 25, 2000.
U.S. Patent and Trademark Office, Official Gazette, vol. 1237, No. 1, pp. 435 and 436, dated Aug. 1, 2000.
U.S. Patent and Trademark Office, Official Gazette, vol. 1237, No. 2, pp. 1669 and 1670, dated Aug. 8, 2000.
U.S. Patent and Trademark Office, Official Gazette, vol. 1237, No. 3, pp. 2845 and 2846, dated Aug. 15, 2000.

* cited by examiner

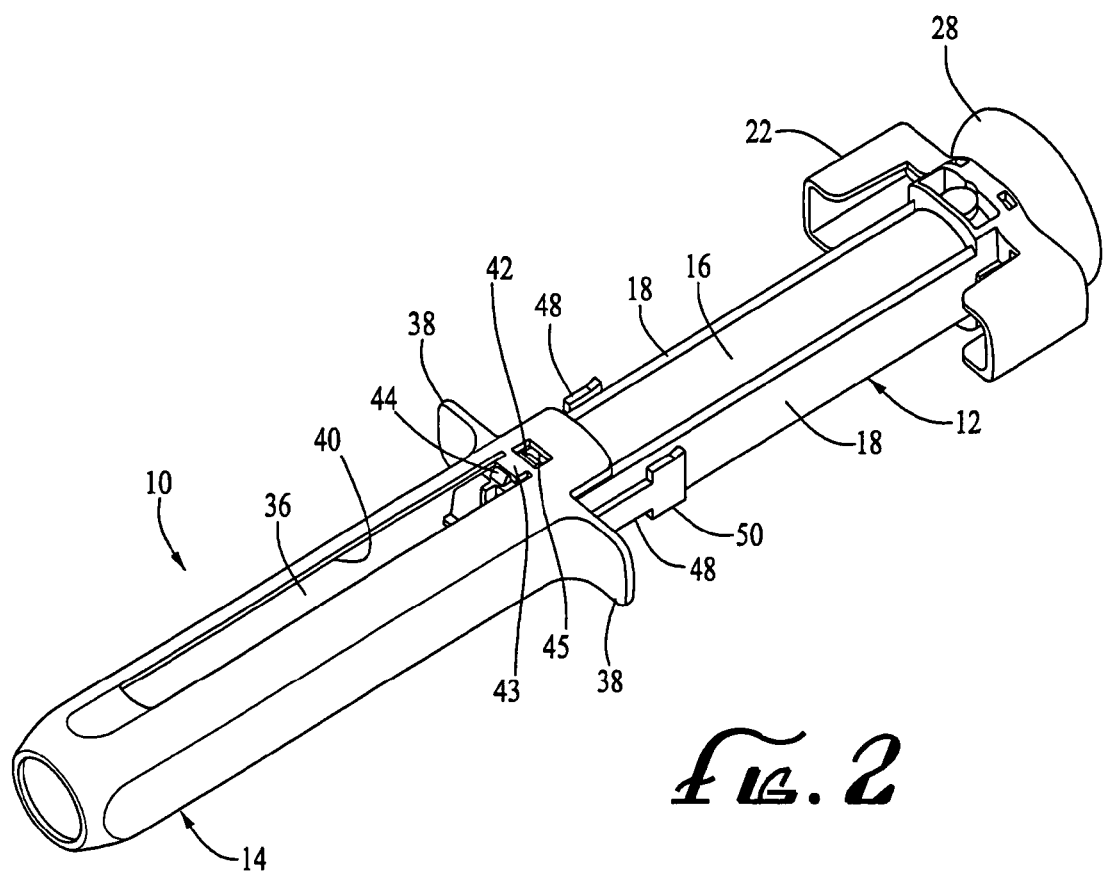

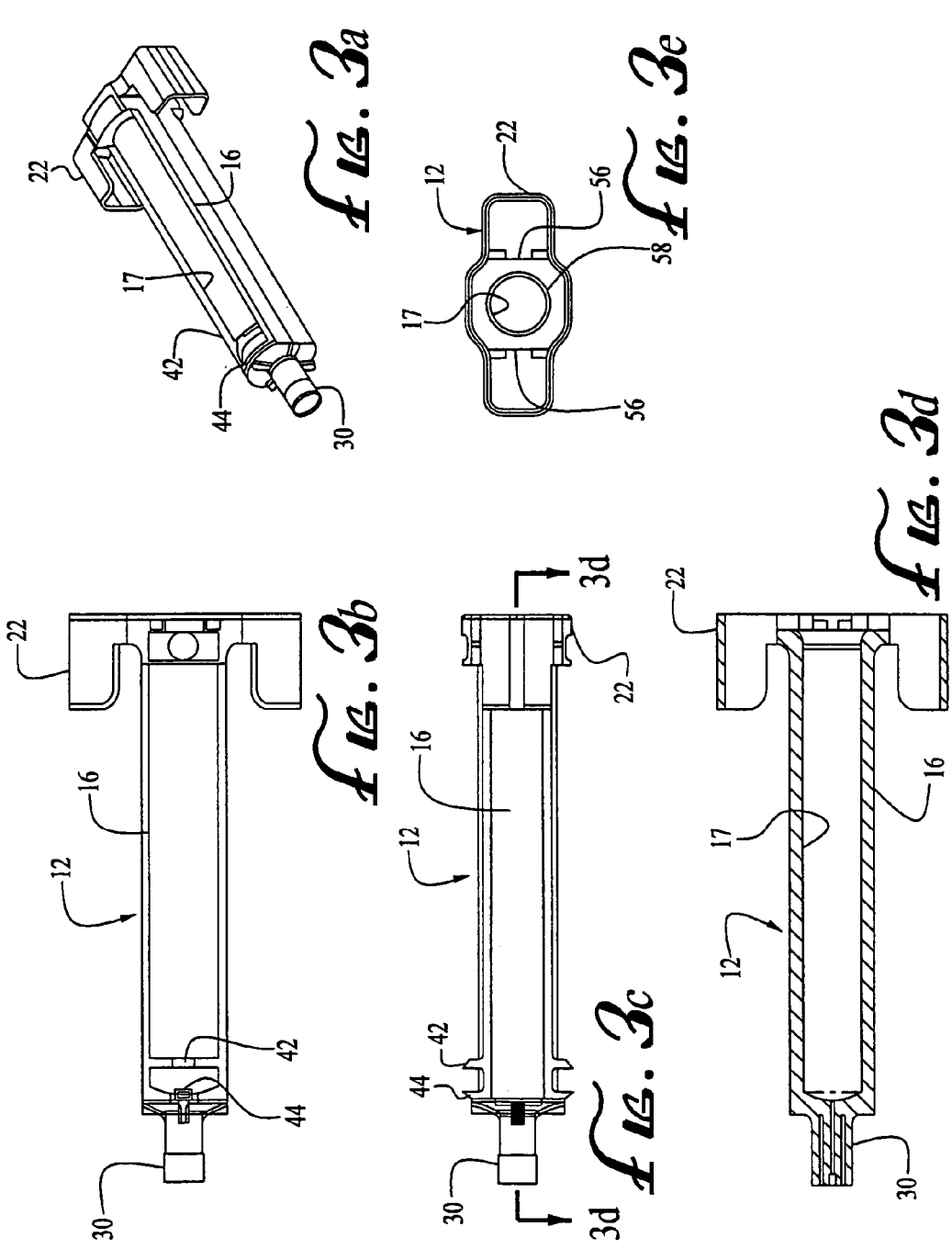

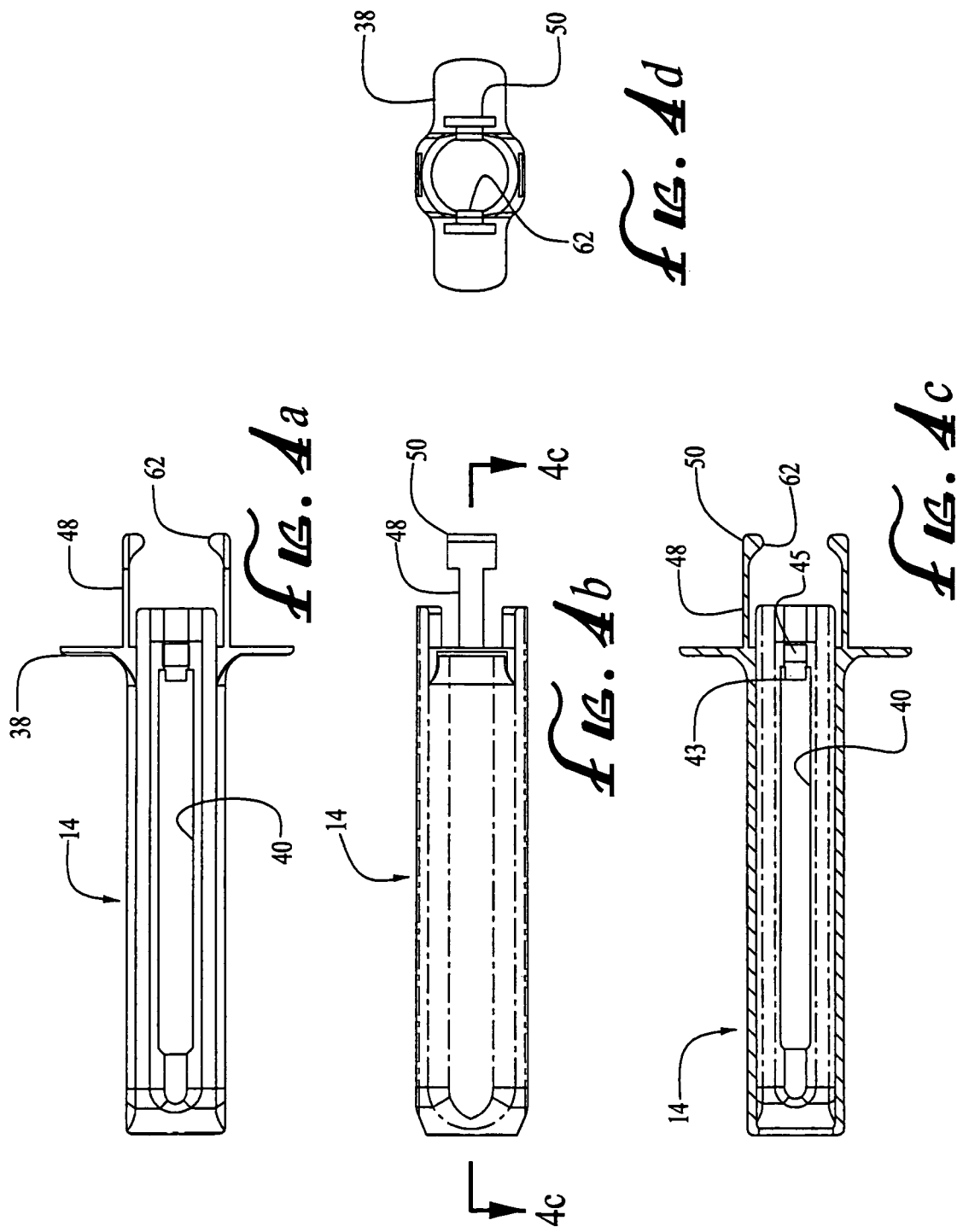

SYRINGE WITH NEEDLE GUARD INJECTION DEVICE

FIELD OF THE INVENTION

The present invention relates generally to injection devices for administering therapeutic agents to patients, particularly to safety devices for syringes, and more particularly to syringe devices that include a needle guard slidably coupled to a syringe for covering a needle of the syringe after use.

BACKGROUND

Medication is often dispensed using a medicine cartridge, such as a syringe, having a barrel with a needle extending from one end and a plunger slidably inserted into the other end. Such cartridges are often referred to as "pre-filled syringes" because they may contain a specific dosage or volume of medication when they are initially provided, as compared to conventional syringes that are furnished empty and filled by the user before making an injection.

Alternatively, a medicine cartridge may be used, such as an ampoule or vial, that includes a penetrable seal instead of a needle on one end of the barrel, and/or a piston rather than a plunger on the other end. Such medicine cartridges are generally inserted into an adapter that includes a hollow body adapted to hold the cartridge, a plunger to engage and move the piston in the cartridge, and a double-ended needle to penetrate the seal and communicate with the interior of the barrel.

Because of the risk of communicable diseases, a number of syringes and adapters have been developed that are intended to prevent accidental needle sticks and/or inadvertent reuse of a syringe. Retractable needle devices have been suggested for this purpose that include a cartridge that allows a needle of the cartridge to be withdrawn into the barrel after medication is dispensed from it. For example, U.S. Pat. No. 4,973,316 discloses a syringe including a barrel having a needle assembly that is slidable within the barrel between an exposed position such that a needle on the assembly extends from the barrel and a retracted position wherein the needle assembly is withdrawn into the barrel. The needle assembly is initially locked in the exposed position, but may be disengaged upon depression of the plunger, whereupon a spring biases the assembly towards the retracted position, thereby withdrawing the needle into the barrel.

Alternatively, syringe holders have been suggested that include a body within which a conventional syringe or cartridge may be received, and a shield that is manually slidable with respect to the body to cover the needle. For example, U.S. Pat. No. 6,030,366 which is assigned to the assignee of the present application, discloses a self-shielding guard that includes a body having an open proximal end for inserting a syringe into a cavity within the body, and a distal end with an opening through which a needle on the syringe may extend once received in the body. A shield is slidable over the body between retracted and extended positions to expose and cover the needle, respectively. With the shield in the retracted position and the needle exposed, an injection may be made, and then the shield may be manually advanced to the extended position. In the extended position, cooperating detents and detent pockets on the body and shield substantially permanently lock together, thereby preventing reuse of the needle, reducing the risk of accidental needle sticks, and/or facilitating disposal of the syringe.

As an alternative to requiring manual extension of a shield to cover a needle, spring-loaded devices have also been developed. These devices often include a body and slidable shield, similar to the manual devices described above, but also may include a spring element to bias the shield to advance and cover the needle. An actuator, such as a button or lever, may be activated by the user to release the shield, thereby allowing the spring element to advance the shield to cover the needle. For example, U.S. Pat. No. 5,695,475 and U.S. Pat. No. 4,923,447 disclose spring-loaded syringe devices that include inner and outer sliding sleeves that include a button slidable in a longitudinal slot to selectively expose and cover a needle on the devices. A spring in the devices biases one of the sleeves to extend and cover the needle, but this bias may be manually overcome to expose the needle. Thus, these devices may not lock the extending sleeve in a covered position, and therefore may risk accidental needle exposure and/or reuse of the needle. In addition, although these devices are spring-driven, their shields may not extend unless they are manually activated by using a button, and therefore are not truly "passive," but require an affirmative decision by a user to activate their safety feature.

Improved automatic syringe and guard assemblies have been developed comprising a body for receiving a syringe, and a guard or shield slideably disposed on the body, and further including detents for maintaining the shield in a first position in which a needle of the syringe is exposed for use, and in a second position covering the needle after use. A suitable spring is disposed between the body and guard to bias the guard and body to the second position. Several examples are U.S. Pat. Nos. 6,623,459 and 6,613,022.

SUMMARY OF THE INVENTION

The present invention is directed to injection devices incorporating both a syringe, such as a pre-filled syringe, or a medicine cartridge, and a guard that covers a needle of the syringe after a medication in the syringe is injected into a patient. More particularly, the present invention is directed to a syringe design which requires no separate body, and a guard disposed on the syringe, and wherein the syringe and guard are each formed of one piece from plastic. The guard includes one or more latch members forming a detent or detents for retaining the guard in a position on the syringe for exposing a needle of the syringe, and wherein the detent or detents may be released upon predetermined depression of a plunger of the syringe to cause the needle of the syringe to be covered by the guard.

In accordance with one aspect of the present invention, an injection device is provided that includes a syringe having a proximal end, a distal end, and a plunger extending from the proximal end. The injection device also includes a guard having a proximal end, a distal end, and a cavity therebetween. The guard is slidably mounted onto the syringe, and includes a latch member that extends proximally from the guard. A needle may extend from the distal end of the syringe. The guard is biased from a first or retracted position wherein the needle of the syringe is exposed, toward a second or extended position wherein the guard covers the needle. The guard may be biased by a spring element between the syringe and guard, such as located in the distal portion of the guard between the guard and the syringe.

First cooperating detents on the syringe and the guard act to retain the guard in the first position. The first cooperating detents preferably include a ledge on the proximal end of the syringe and a catch on a latch member extending from the guard. Here, the ledge and catch engage one another to retain the guard in the first position. As the plunger is advanced within the syringe, the plunger engages the latch member and releases the first cooperating detents, whereupon the guard slides toward the second position. Second cooperating detents are provided on the syringe and guard to retain the guard in the second position. The second cooperating detents preferably include a detent pocket on the guard and a corresponding tab on the syringe.

More particularly, the syringe comprises a central body having a cylindrical opening for containing medicine and a plunger, and one or more elongated rectangular members or rails disposed on opposite sides of the body and which rails are configured to fit and slide within the guard. The proximal end of the syringe can include suitable gripping surfaces, and the distal end includes a hub to which a needle may be attached such as by threads or a luer lock.

Optionally, the guard may also include a window or slot that extends axially along the guard. When the slot is present on the guard, the syringe may include a stop tab configured to travel within the slot. The stop tab and slot may be configured to limit the proximal and distal movement of the syringe relative to the guard. For example, the stop tab may abut the distal edge of the window when the guard is in the first position to prevent further distal movement of the syringe (or proximal movement of the guard). Similarly, the stop tab may abut the proximal edge of the window when the guard is in the second position to prevent further proximal movement of the syringe (or distal movement of the guard). In addition, the guard may also include a set of finger flanges or grips usable for controlling the movement and speed of advancement or sliding of the guard between the first and second positions with respect to the syringe.

Other advantages and features of the present invention will become apparent from consideration of the following description taken in conjunction with the accompanying drawings.

BRIEF DESCRIPTION OF THE DRAWINGS

FIG. 2 is another perspective view, but illustrating the guard in an extended position with respect to the syringe for covering the needle thereof.

FIG. 3a is a prospective view of the syringe.

FIG. 3b is a top plan view of the syringe.

FIG. 3c is a side elevational view.

FIG. 3d is a cross-sectional view taken along line 3d-3d of FIG. 3c.

FIG. 3e is a proximal end view of the syringe.

FIG. 4a is a top plan view of the guard.

FIG. 4b is a side elevational view.

FIG. 4c is a cross-sectional view taken along a line 4c-4c of FIG. 4b.

FIG. 4d is an enlarged proximal end elevational view.

DETAIL DESCRIPTION

Figure 1:
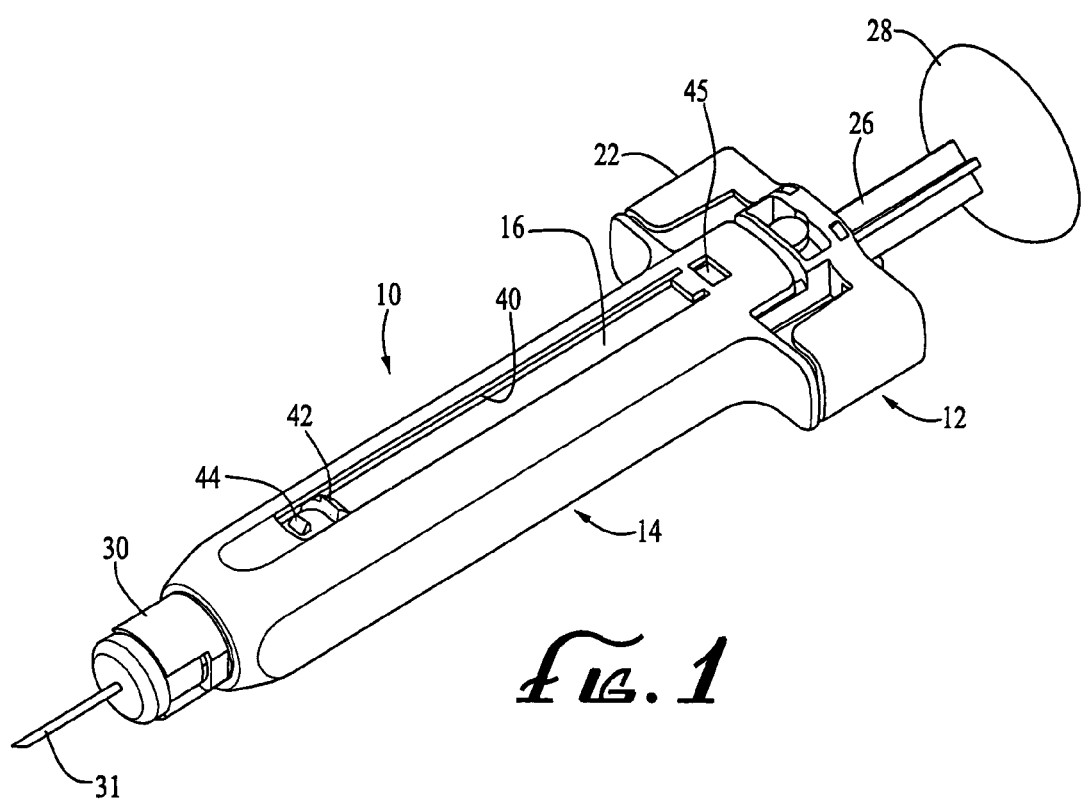
FIG. 1 is a perspective view of a syringe and guard of the present invention with the guard in a retracted position exposing a needle of the syringe.

Turning now to the drawings, and first to FIGS. 1 and 2, a syringe and guard assembly 10 is illustrated and comprises a syringe 12 and guard 14. The syringe 12 includes a central body 16 which is a hollow cylinder on the inside and may be cylindrical on the outside as seen in FIG. 2. The syringe 12 includes a pair of longitudinally extending members or rails 18 which are integrally formed on opposite sides of the body 16 as seen in FIG. 2. The proximal end of the syringe 12 includes a gripping member 22. The syringe 12 further includes a conventional plunger 26 with a thumb pad 28. The plunger 26 includes the usual flexible or rubber piston (not shown) on the distal end thereof which slides within the smooth wall interior cylindrical surface of the barrel 16 to dispense medication from the distal end 30 of the syringe 12 through a needle. A needle 31 is attached to the distal end 30. Tab or stop 44 limits distal movement.

The guard 14 is configured to slide between the retracted position shown in FIG. 1 and the extended position shown in FIG. 2, and has elongated rectangular interior sides, only side 36 being seen in FIG. 2, to appropriately mate with the elongated rails 18 of the syringe 12. The guard 14 includes finger grips 38, and preferably includes a window 40 within which a tab 42 from the barrel 16 of the syringe 12 forming a detent may lie. The tab 42 on the syringe limits distal motion of the guard 14 as best seen in FIG. 2. The guard includes a cross-member 43 defining a slot 45. When the guard is in the fully extended position as seen in FIG. 2, the tab 42 of the syringe snaps into the slot 45 to maintain the guard and syringe in the needle protected position seen in FIG. 2.

Reference is now made to the drawings of the syringe and guard in FIGS. 3 and 4. The guard 14 further includes one or more latches 48 having respective flanges or catches 50 forming detents on the proximal end of the guard 14 for engaging cooperating detent surfaces or ledges in the proximal end of the syringe as described below. Turning to FIG. 3e, the proximal end of the syringe 12 is illustrated particularly showing slots 56 on opposite sides of the barrel 16 into which the arms of the latches 48 can rest with the flanges 50 hooked on the rear proximal surface 58 of the proximal end of the syringe 12 when the guard 14 is fully retracted onto the syringe 12 as seen in FIG. 1. The flanges 50 of the latches 48 have inwardly extending fingers 62 (see FIGS. 4a & 4d) which extend further proximally and are engageable by a rounded outer surface of the thumb pad 28 as the plunger approaches its far distal position in dispensing medicine. By the pad 28 engaging the fingers 62, the latches 48 are deflected outwardly, thereby releasing the flanges 50 from the surface 58 and out of the slots 56 to allow the guard 14 to automatically move to the extended position with respect to the syringe as seen in FIG. 2 under the bias of a coil spring which is described below.

Turning more specifically to the syringe FIGS. 3a-3e, the same show the structure of the syringe in more detail, particularly the tab 42, stop 44, and slots 56 which the arms of latches 48 (FIG. 4) hook on as seen in FIGS. 4a and 4d. At the proximal end of the syringe, these slots 56 allow the latches 48 to move inwardly so that the flanges 50 can readily hook on the rear proximal surface 58 of the proximal end of the syringe 12 when the guard 14 is fully retracted onto the syringe as seen in FIG. 1.

After an injection is made, the guard and syringe move, preferably via spring action from a spring (not shown) between the distal ends of the syringe and guard, to the relative positions shown in FIG. 2. The tab 42 locks in the slot 45 to fully lock the guard 14 in the position covering the needle of the syringe. Stop 44 and cross member 43 limit the distal movement.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An injection device, comprising:

a plastic syringe comprising a proximal end, a distal end, and a plunger extending from the proximal end, the syringe comprising a body having a hollow cylindrical interior for receiving a medicine and the plunger, and a pair of rectangular longitudinal rails on opposite sides of the body, and a gripping member on the proximal end, the gripping member having slots on opposing sides of the body, a plastic guard slidably attached to the syringe and having a proximal end and a distal end, the guard being biased from a first position wherein the distal end of the syringe is exposed toward a second position wherein the guard covers the distal end of the syringe, the guard having an interior configuration for mating with the longitudinal rails of the syringe and being slideable thereon, cooperating detents on the syringe and guard for retaining the guard in the first position and in the second position, the cooperating detents including a first tab and a second tab formed on the body of the syringe adjacent the distal end and axially spaced from one another, a window longitudinally extending along the guard and a slot formed in the guard adjacent the proximal end of the guard in spaced relation with the window, wherein a cross-member defines a distal edge of the slot and a proximal edge of the window, the first tab engages the distal edge of the slot in the guard for limiting proximal motion of the guard when in the second position, the second tab engages a distal edge of the window for limiting proximal motion of the guard when in the first position and engages the proximal edge of the window for limiting distal movement of the guard when in the second position, wherein the cross-member interposes the first and second tabs when the guard is in the second position, and latch members extending proximally from the guard through the slots in the gripping member and having laterally extending flanges to engage a proximal end of the gripping member, the latch members having inwardly extending rounded fingers at a proximal end that are engageable by a rounded outer cam surface of a thumb pad of the plunger as the plunger is advanced into the syringe for moving the latch members to release the latch members from the gripping member whereupon the guard may slide toward the second position.

2. The device of claim 1, further comprising a spring coupled to the guard and the syringe for biasing the guard toward the second position.

3. The device of claim 1, wherein the first and second tabs are configured to travel within the window.

4. The device of claim 3, wherein the second tab and the proximal edge of the window prevent the guard from advancing distally beyond the second position.

5. The device of claim 3, wherein the second tab and the distal edge of the window prevent the guard from moving proximally beyond the first position.

6. The device of claim 1, wherein the cooperating detents for retaining the guard in the first position comprise a ledge on the proximal end of the syringe and a catch comprising a lateral edge on one of the flanges of the latch members, and wherein the guard is retained in the first position when the catch engages the ledge.

7. The device of claim 6, wherein the fingers of the latch members are located distally from the proximal end of the latch members.

8. The device of claim 1, wherein the cooperating detents comprise the slot on the guard and the first tab on the syringe for preventing the guard from being moved from the second position toward the first position.

9. The device of claim 1, wherein the guard further comprises a set of finger flanges for facilitating controlling movement of the guard from the first position toward the second position.

* * * * *